United States Patent
Sutphen

(10) Patent No.: US 7,964,408 B1
(45) Date of Patent: Jun. 21, 2011

(54) LYSOPHOSPHOLIPIDS AS BIOMARKERS OF OVARIAN CANCER

(75) Inventor: Rebecca Sutphen, Madeira Beach, FL (US)

(73) Assignee: University of South Florida, Tampa, FL (US)

( * ) Notice: Subject to any disclaimer, the term of this patent is extended or adjusted under 35 U.S.C. 154(b) by 1046 days.

(21) Appl. No.: 10/908,484

(22) Filed: May 13, 2005

Related U.S. Application Data

(60) Provisional application No. 60/570,675, filed on May 13, 2004.

(51) Int. Cl.
*G01N 33/00* (2006.01)

(52) U.S. Cl. .......................................... 436/64

(58) Field of Classification Search ................ 436/6
See application file for complete search history.

(56) References Cited

U.S. PATENT DOCUMENTS

| | | | |
|---|---|---|---|
| 6,248,553 B1 * | 6/2001 | Small et al. | 435/25 |
| 6,294,349 B1 | 9/2001 | Streckfus et al. | |

OTHER PUBLICATIONS

X. Fang et al., "Lysophospholipid Growth Factors in the Initiation, Progression, Me~stases, and Management of Ovarian Cancer", Annals New York Academy of Sciences, pp. 188-208.*

A. Tokumura, "Physiological and Pathophysiological Roles of Lysophosphatidic Acids Produced by Secretory Lysophospholipase D in Body Fluids", Biochimica et Biophysica Acta, 1982, (2002), pp. 18-25.*

K. Sawada, et al., ~Lysophosphatidic Acid Induces Focal Adhesion Assembly Through Rho/Rho-Associated Kinase Pathway in Human Ovarian Cancer Cells, Gynecologic 87, 252-259 2002.*

Luo et al.; he Serum Concentration of Human Kallikrein 10 Represents a Novel Biomarker for Ovarian Cancer Diagnosis and Prognosis; Cancer Research; 63, 807-811; Feb. 15, 2003.

Griffiths et al. 2001. "Electrospray and Tandem Mass Spectrometry in Biochemistry." Biochem. vol. 355. pp. 545-561.

* cited by examiner

*Primary Examiner* — Sam P Siefke
(74) *Attorney, Agent, or Firm* — Robert Varkonyi; Smith & Hopen, P.A.

(57) ABSTRACT

A method of using a bioactive lysophospholipid (LL) as a biomarker for detecting the presence and recurrence of ovarian cancer. Subspecies of LL, such as lysophosphatidic acid (LPA), lysophosphatidylinositol (LPI), lysophosphatidylcholine (LPC), and lysosphingolipid sphinsosine-1-phosphate (S1P), are used alone or in conjunction to increase the specificity and sensitivity of the assay.

18 Claims, 5 Drawing Sheets

Fig.1

Clinical Data for Patients with Ovarian Cancer
(N = 117)

| Characteristics | Stages I and II (N = 29) | Stages III and IV (N = 88) | Percentage (N=117) |
|---|---|---|---|
| Age, median (range), yr | 60 (32 – 77) | 59 (26 – 80) | |
| Stages | | | |
| I | 18 | - | 15.4% |
| II | 11 | - | 9.4% |
| III | - | 74 | 63.2% |
| IV | - | 14 | 12.0% |
| Grades | | | |
| 1 | 10 | 11 | 18.0% |
| 2 | 8 | 21 | 24.8% |
| 3 | 11 | 55 | 56.4% |
| Ungraded | 0 | 1 | 0.8% |
| Histologic types | | | |
| Serous | 12 | 61 | 62.4% |
| Endometrioid | 11 | 7 | 15.4% |
| Mixed | 0 | 8 | 6.8% |
| Mucinous | 3 | 2 | 4.3% |
| Primary Peritoneal | 0 | 4 | 3.4% |
| Clear cell | 2 | 2 | 3.4% |
| Transitional cell | 1 | 2 | 2.6% |
| Brenner | 0 | 2 | 1.7% |
| Treatment status | | | |
| Preoperative | 10 | 35 | 38.5% |
| Postoperative | 19 | 53 | 61.5% |

Fig. 2

Means (Standard Deviations) for LPL in Controls and Preoperative Case Samples by Stage (in μM)

| Substance | Controls (N = 27) | Stage I (N = 7) | Stage II (N = 3) | Stage III (N = 31) | Stage IV (N = 4) |
|---|---|---|---|---|---|
| 16:0-LPA ++++ | 00.14 (00.13) | 00.52 (00.39) | 00.62 (00.35) | 00.73 (00.73) | 00.37 (00.14) |
| 18:0-LPA ++++ | 00.13 (00.10) | 00.47 (00.42) | 00.29 (00.19) | 00.53 (00.51) | 00.23 (00.03) |
| 18:1-LPA ++++ | 00.17 (00.14) | 00.37 (00.27) | 00.46 (00.29) | 00.47 (00.36) | 00.32 (00.06) |
| 18:2-LPA ++++ | 00.16 (00.14) | 00.29 (00.26) | 00.31 (00.08) | 00.46 (00.39) | 00.34 (00.09) |
| 20:4-LPA ++++ | 00.22 (00.16) | 00.71 (00.47) | 00.31 (00.13) | 00.50 (00.31) | 00.55 (00.17) |
| 22:6-LPA +++ | 00.09 (00.07) | 00.20 (00.12) | 00.16 (00.09) | 00.24 (00.24) | 00.16 (00.03) |
| 16:0-A-LPA + | 00.11 (00.08) | 00.15 (00.07) | 00.08 (00.05) | 00.18 (00.08) | 00.19 (00.04) |
| 18:0-A-LPA ++ | 00.04 (00.06) | 00.07 (00.08) | 00.10 (00.06) | 00.08 (00.06) | 00.07 (00.03) |
| 16:0-An-LPA ++++ | 00.07 (00.05) | 00.18 (00.11) | 00.11 (00.01) | 00.15 (00.10) | 00.17 (00.05) |
| 18:0-An-LPA ++++ | 00.03 (00.04) | 00.07 (00.03) | 00.11 (00.06) | 00.09 (00.07) | 00.04 (00.03) |
| Total A-LPA ++++ | 00.25 (00.12) | 00.48 (00.13) | 00.40 (00.10) | 00.50 (00.19) | 00.47 (00.04) |
| Total LPA ++++ | 00.90 (00.43) | 02.57 (00.94) | 02.15 (00.71) | 02.93 (01.77) | 01.97 (00.27) |
| 16:0-LPA/20:4-LPA ++++ | 00.35 (00.17) | 01.23 (00.52) | 00.92 (00.43) | 01.23 (00.70) | 00.93 (00.15) |
| 16:0-LPI +++ | 00.49 (00.47) | 00.75 (00.59) | 01.88 (01.34) | 01.00 (00.64) | 00.90 (00.23) |
| 18:0-LPI +++ | 00.50 (00.43) | 00.87 (00.71) | 01.77 (02.49) | 01.89 (02.05) | 00.70 (00.25) |
| 20:4-LPI ++++ | 00.51 (00.43) | 01.35 (00.78) | 00.93 (00.95) | 01.36 (00.84) | 01.36 (00.24) |
| Total LPI ++++ | 01.51 (00.79) | 02.98 (01.57) | 04.58 (02.71) | 04.25 (02.81) | 02.96 (00.33) |
| 16:0-LPC | 52.37 (25.63) | 70.65 (30.07) | 55.98 (26.57) | 52.98 (30.62) | 48.10 (21.15) |
| 18:0-LPC | 15.63 (08.28) | 21.00 (09.90) | 17.23 (10.98) | 14.90 0(9.56) | 14.81 (06.57) |
| 18:1-LPC | 16.89 (07.27) | 21.71 (10.42) | 18.97 (13.40) | 17.06 (11.40) | 17.61 (10.02) |
| 18:2-LPC + | 20.21 (07.63) | 17.50 (07.72) | 16.63 (12.86) | 15.12 (08.99) | 16.34 (10.36) |
| 20:0-LPC | 00.21 (00.07) | 00.25 (00.12) | 00.19 (00.08) | 00.33 (00.41) | 00.20 (00.14) |
| 20:4-LPC | 10.44 (03.10) | 11.60 (04.95) | 09.38 (01.56) | 10.11 (04.72) | 10.36 (03.41) |
| 22:6-LPC + | 05.89 (02.24) | 10.41 (06.00) | 06.98 (04.63) | 08.56 (05.96) | 09.65 (05.96) |
| Total LPC | 121.65 (47.22) | 153.12 (60.02) | 125.37 (68.84) | 119.07 (64.40) | 117.05 (57.06) |
| S-1-P +++ | 00.36 (00.27) | 00.77 (00.42) | 00.50 (00.43) | 00.66 (00.48) | 00.65 (00.26) |

*P* values show significance levels for differences observed between healthy controls (N = 27) and all ovarian cancer cases for who preoperative samples were available (N = 45).

Total LPA Levels (μM) in Preoperative Case Samples and Controls

Fig. 5

Means (Standard Deviations) for Paired Preoperative and Postoperative Samples
(N = 22)

| Substance | Preoperative Mean | Postoperative Mean |
| --- | --- | --- |
| 16:0-LPA | 00.85 (00.84) | 00.50 (00.28) |
| 18:0-LPA + | 00.64 (00.61) | 00.33 (00.24) |
| 18:1-LPA | 00.55 (00.41) | 00.36 (00.29) |
| 18:2-LPA | 00.39 (00.43) | 00.38 (00.27) |
| 20:4-LPA | 00.55 (00.39) | 00.47 (00.41) |
| 22:6-LPA + | 00.28 (00.28) | 00.12 (00.09) |
| 16:0-A-LPA | 00.17 (00.09) | 00.16 (00.15) |
| 18:0-A-LPA | 00.10 (00.06) | 00.09 (00.10) |
| 16:0-An-LPA | 00.14 (00.07) | 00.14 (00.11) |
| 18:0-An-LPA | 00.09 (00.07) | 00.06 (00.07) |
| Total A-LPA | 00.50 (00.18) | 00.44 (00.27) |
| Total LPA + | 03.27 (01.98) | 02.16 (01.04) |
| 16:0-LPA/20:4-LPA + | 01.41 (00.78) | 00.97 (00.51) |
| 16:0-LPI | 01.21 (00.91) | 01.24 (01.40) |
| 18:0-LPI | 02.06 (02.32) | 01.28 (01.37) |
| 20:4-LPI | 01.38 (00.99) | 01.34 (01.06) |
| Total LPI | 04.65 (03.21) | 03.86 (02.05) |
| 16:0-LPC | 52.61 (30.34) | 67.32 (36.06) |
| 18:0-LPC | 13.72 (08.62) | 18.96 (10.18) |

LYSOPHOSPHOLIPIDS AS BIOMARKERS OF OVARIAN CANCER

CROSS REFERENCE TO RELATED APPLICATION

This application claims priority to U.S. Provisional Patent Application No. 60/570,675, entitled, "Lysophosphatidylcholine as a Biomarker of Ovarian Cancer," filed by the same inventor on May 13, 2004 which is incorporated herein by reference.

BACKGROUND OF THE INVENTION

The mortality rate for women with ovarian cancer is very high, with an estimated 14,300 deaths from ovarian cancer in 2003 in the United States. More than two-thirds of patients have late stage metastatic disease at initial diagnosis with a 5-year survival rate of approximately 20-30%. Conversely, the long-term survival rate approaches 90% at early stages. There is currently no proven effective method for early detection of ovarian cancer through biomarkers, imaging, or other means. The most common biomarker for ovarian cancer is CA 125 which lacks specificity and is elevated in only about 50% of stage I ovarian cancer cases. Proteomic patterns derived from surface-enhanced laser desorption/ionization mass spectroscopy analysis have recently shown promise for early ovarian cancer detection but further studies regarding their reproducibility and reliability for early detection and screening are needed.

SUMMARY OF INVENTION

Ovarian cancer is a disease associated with a high mortality mainly because it currently escapes detection at early stages. Identification of an effective biomarker for early detection would improve survival. The present invention documents statistically significant differences in LPL levels between preoperative samples of ovarian cancer patients and those of healthy controls. The study also confirms that statistically significant elevations in LPL levels are present in patients with early stage disease. Thus, the findings support the utility of LPL, especially LPA, as biomarkers for early detection of ovarian cancer.

In a general embodiment, the present invention includes a method of detecting ovarian cancer in a subject comprising the steps of obtaining a biological sample from said subject and measuring the total amount of at least one lysophospholipid present within the sample. The presence of elevated levels of the at least one lysophospholipid is indicative of the presence of ovarian cancer. The at least one lysophospholipid is selected from the group consisting of lysophosphatidic acid (LPA), lysophosphatidylinositol (LPI), lysophosphatidylcholine (LPC), and lysosphingolipid sphinsosine-1-phosphate (S1P).

The method of the present invention can be employed preoperatively, to diagnose the presence of ovarian cancer, or postoperatively to detect the recurrence of ovarian cancer.

In an alternate embodiment the present invention includes a method of detecting ovarian cancer in a subject comprising the steps of obtaining a biological sample from said subject, measuring the amount of lysophsphatidic acid (LPA) present in the sample as well as measuring the total amount of at least one lysophospholipid subspecies present within the sample whereby the presence of elevated levels of the total lysophosphatidic acid (LPA) and least one lysophospholipid subspecies is indicative of the presence of ovarian cancer. In this alternate embodiment, the at least one lysophospholipid subspecies is selected from the group consisting of lysophosphatidylinositol (LPI), lysophosphatidylcholine (LPC), and lysosphingolipid sphinsosine-1-phosphate (S1P).

As with the previous embodiment, the method can be employed preoperatively, to diagnose the presence of ovarian cancer, or postoperatively to detect the recurrence of ovarian cancer.

Plasma samples were collected from ovarian cancer patients and healthy control women in Hillsborough and Pinellas counties, Florida, and processed at the H. Lee Moffitt Cancer Center and Research Institute at the University of South Florida (Moffitt). One hundred seventeen (117) case patients with epithelial ovarian cancer and 27 healthy control subjects participated in the study. Blinded LPL analysis, including 23 individual LPL species, was performed at the Cleveland Clinic Foundation, using an electrospray ionization mass spectrometry-based method. LPL levels were transmitted to Moffitt where clinical data were reviewed and statistical analyses performed.

There were statistically significant differences between preoperative case samples (N=45) and control samples (N=27) in the mean levels of total LPA, total lysophosphatidylinositol (LPI), sphingosine-1-phosphate (S1P) and individual LPA species, as well as the combination of a number of LPL species. The combination of 16:0-LPA and 20:4-LPA yielded the best discrimination between preoperative case samples and control samples, with 93.1% correct classification, 91.1% sensitivity and 96.3% specificity. In 22 cases with both preoperative and postoperative samples, the postoperative levels of a number of LPL, including S1P, total LPA and LPC levels and some individual species of LPA and LPC, were significantly different from preoperative levels.

BRIEF DESCRIPTION OF THE DRAWINGS

For a fuller understanding of the nature and objects of the invention, reference should be made to the following detailed description, taken in connection with the accompanying drawings, in which:

FIG. 1 shows the ages, stages, grades, histologic subtypes and treatment status of the 117 ovarian cancer patients who participated in the study.

FIG. 2 shows the statistically significant differences between preoperative case samples (N=45) and control samples (N=27) in the mean levels of several individual LPA species, the combination of 16:0-LPA/20:4-LPA, total LPA, total LPI and S1P.

FIG. 5 shows the postoperative levels of total LPA, total LPC, 22:6-LPA, 18:0-LPA, the combination of 20:4-LPA/22:6-LPA, 20:4-LPC and 18:2-LPC were significantly lower than preoperative levels (P=0.03, 0.05, 0.02, 0.04, 0.03 0.02, 0.003 and 0.03, respectively).

DETAILED DESCRIPTION OF THE PREFERRED EMBODIMENT

Figure 3:
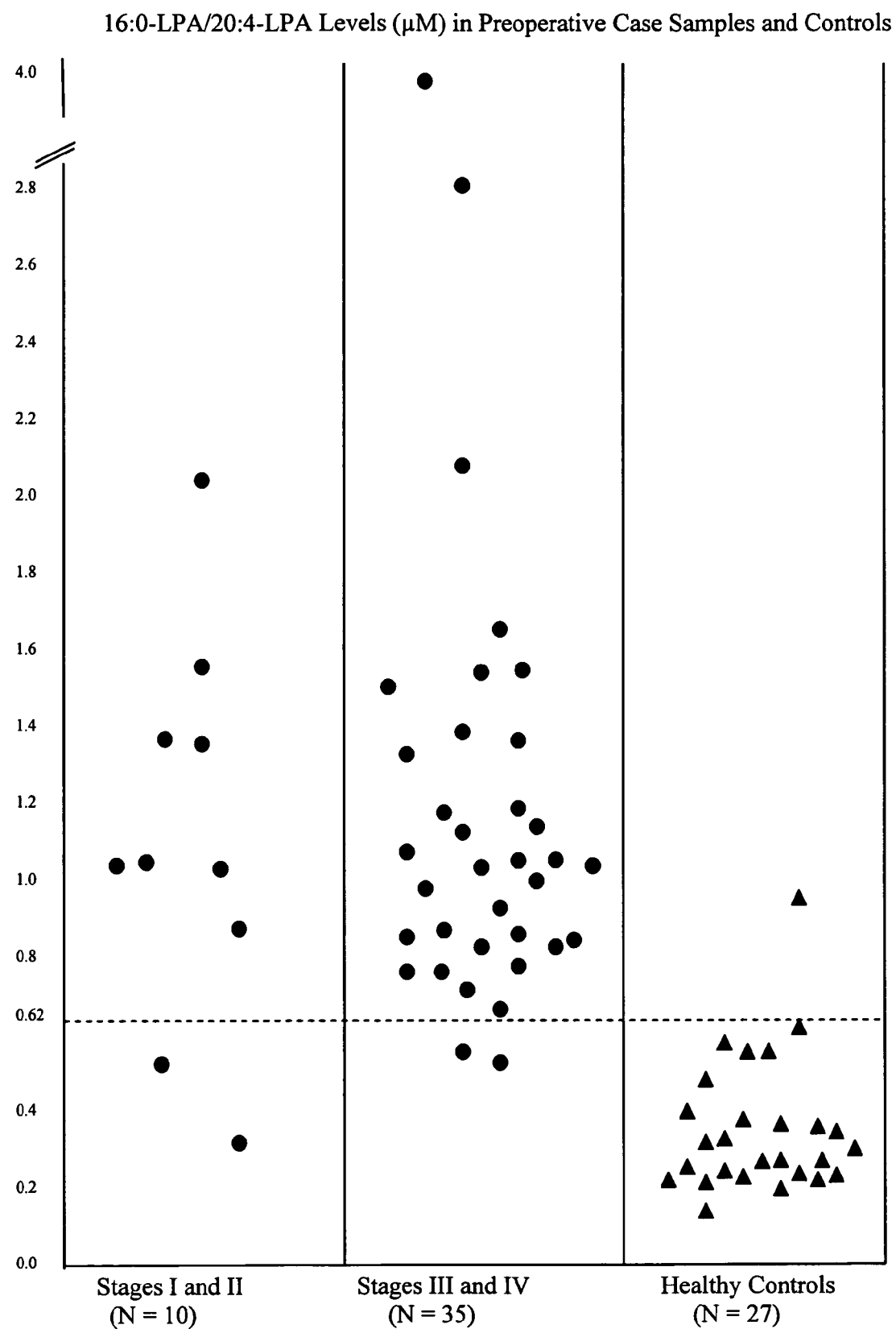
FIG. 3 indicates the best discrimination between samples obtained preoperatively from ovarian cancer patients and those from healthy controls was achieved by the combined levels of 16:0-LPA and 20:4-LPA, with 93.1% correct classification, 91.1% sensitivity and 96.3% specificity.

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

Lysophosphatidic acid (LPA), a bioactive lysophospholipids (LPL), has been proposed as a biomarker for the early detection of ovarian cancer. Pervious studies have shown elevated levels in the plasma of ovarian cancer patients compared with controls using gas chromatography-based analysis. LPA appears to have a role in ovarian cancer proliferation, cell survival, angiogenesis and metastasis.

The present invention LPA and related LPLs were measured in 117 case patients with epithelial ovarian cancer and 27 healthy control subjects. Electrospray ionization/mass spectrometry (ESI/MS) methods were used in place of gas chromatography. Statistically significant differences existed between preoperative case samples (N=45) and control samples (N=27) in the means levels of total LPA, total lysophosphatidylinositol (LPI), sphingosine-1-phosphate (s1P) and the following LL subspecies: 20:4-LPA, 22:6-LPA, 16:0-LPA, 18:0-LPA, 18:1-LPA, 18:2-LPA, 16:0-alkenyl-LPA, 16:0-alkyl-LPA, 18:0-alkenyl-LPA, 18:0-alkyl-LPA, total alkenyl- and alkyl-LPA, the combination of 20:4-LPA/16:0-LPA, 20:4-LPI, 16:0-LPI, 18:0-LPI, 22:6-LPC, and 18:2-LPC (P=0.001, 0.0001, 0.0003, 0.0001, 0.0004, 0.0001, 0.0003, 0.002, 0.03, 0.0001, 0.002, 0.0002, 0.02, 0.0001, 0.0001, 0.0001, 0.0001, 0.0001, 0.0001, and 0.003, respectively).

The combination of 20:4-LPA and 16:0-LPA yielded the best discrimination between preoperative case samples and control samples, with 90.4% correct classification, 91.1% sensitivity and 89.3% specificity. Total LPA achieved 88.9% correct classification, with 91.1% sensitivity and 85.2% specificity. There were also statistically significant differences between preoperative case samples (N=45) and postoperative case samples (N=94) in mean levels of the following LL⊕mean X in preoperative cases (95% CI=x–x) and mean X in postoperative cases (95% CI=x–x) (P<.x). In 22 cases with both preoperative and postoperative samples, the postoperative levels of total LPA, S1P, total LPC, 22:6-LPA, 18:0-LPA, the combination of 20:4-LPA/22:6-LPA, 20:4-LPC and 18:2-LPC were significantly lower than preoperative levels (P=0.3, 0.03, 0.05, 0.02, 0.04, 0.03, 0.02, and 0.003 respectively. Accordingly, total LPA, total LPI, S1P and various subspecies of LPA, LPI and LPC are useful as diagnostic and prognostic biomarkers of ovarian cancer.

Lysophosphatidic acid (LPA) has been proposed as a sensitive biomarker. However, studies investigating the utility of LPA as a biomarker for early detection of ovarian cancer have yielded conflicting results. Preliminary findings from a study which included 48 healthy controls and 48 women with ovarian cancer showed that plasma LPA levels (measured by gas chromatography) were elevated in patients with ovarian cancer (P<0.001). Importantly, elevated levels were detected in early-stage ovarian cancers compared with controls. The study also compared available CA125 values with LPA levels and results suggested that plasma LPA may be a more sensitive marker for ovarian cancer, particularly for stage I disease.

A recent Korean study of only 3 pairs of samples also showed differences between ovarian cancer cases and controls. However, in another study where LPA levels were measured in plasma samples from 32 patients with ovarian cancer and 32 healthy controls using a liquid chromatography/mass spectroscopy assay, results showed no significant elevation in plasma LPA levels in ovarian cancer patients compared to controls, raising questions about the utility of plasma LPA levels for early detection of ovarian cancer.

LPA is present in the ascitic fluid of patients with ovarian cancer and may function as an autocrine factor, contributing to ovarian cancer proliferation, cell survival, angiogenesis and metastasis. Lysophosphatidylinositol (LPI), a related LPL to LPA, has also been found at increased levels in ascites fluid and plasma of ovarian cancer patients compared with controls and has been shown to display signaling properties in cellular systems. Thus, LPI also has utility as a biomarker of ovarian cancer, and data shows that measuring LPI in addition to LPA may increase the sensitivity and/or specificity of the test. Both LPA and LPI represent various subspecies with different fatty acid chains. In addition, the fatty acid chain may link to the glycerol backbone through different chemical linkages resulting in various subclasses (i.e., acyl-(LPA), alkyl-(A-LPA), and alkenyl-(An-LPA). Findings of a study to evaluate the discriminating ability of LPA and LPI subspecies for ovarian cancer identification compared with total LPA and LPI suggested that subspecies with unsaturated fatty acid chains may be associated with late-stage or recurrent ovarian cancer. Other LPL that have been proposed to have a biologic role in ovarian cancer and be potentially useful as biomarkers of the disease include lysophosphatidylcholine (LPC), which has also been shown to be elevated in the plasma of ovarian cancer patients, and the lysosphingolipid sphingosine-1-phosphate (S1P) which is known to have both extracellular and intracellular signaling properties.

To further explore the potential of LPA, LPI, LPC and S1P as biomarkers for ovarian cancer detection, we measured plasma LPL levels (including subspecies of LPA, LPI and LPC) in women with ovarian cancer and healthy controls, using electrospray ionization mass spectrometry (ESI/MS) methods. This assay allows simultaneous detection and quantitation of different species of LPL with at least 10 times more sensitivity than the previous gas chromatography method.

Example

Patient-derived biologic specimens were collected under protocols approved by the Institutional Review Board of the University of South Florida and all participants provided written informed consent.

Whole blood samples were obtained preoperatively in EDTA tubes by routine venipuncture of women undergoing surgery for suspected ovarian cancer in Hillsborough and Pinellas counties, Florida between Dec. 13, 2000 and Oct. 30, 2002. All women ages 18-80 undergoing surgery for suspected ovarian cancer in the two counties during the defined period were regarded as eligible for entry into the study. No patients who were asked refused to participate. Of the preoperative samples obtained, 45 were from women who were later confirmed to have ovarian cancer or primary peritoneal cancer (ovarian cancer patients) (median age 60 years, range 33-79). Samples were obtained postoperatively from ovarian cancer patients from the same eligibility pool (N=94, median age 59, range 26-80), including 22 patients who had contributed a preoperative sample and 72 who had not. Whole blood samples from control subjects were collected concurrently from healthy women from the same counties who reported no history of cancer, gynecologic disease, oophorectomy or family history of breast/ovarian cancer (N=27, median age 45, range 22-79). Whole blood specimens were obtained from a total of 117 ovarian cancer patients, including 18 patients with stage I disease, 11 with stage II disease, 74 with stage III disease and 14 with stage IV disease. Among the 45 patients for whom a preoperative sample was available, there were 7 patients with Stage I disease, 3 with Stage II disease, 31 with stage III disease and 4 with stage IV disease. Cancer diagnosis was confirmed for all cases by review of pathology records by a single ovarian cancer expert. Clinical stage was determined according to International Federation of Gynecologists and Obstetricians criteria, and the histologic subtype was evaluated according to the World Health Organization classification.

Sample Collection

LPA is produced and released by activated platelets during coagulation and therefore is a normal constituent of serum, but it is present only at very low levels in whole blood or fresh platelet-poor plasma from healthy individuals. To prevent platelet activation and phospholipase activity, whole blood samples were collected via routine venipuncture in EDTA-containing tubes. Since LPLs are metabolites and levels may change during incubation, it is important that sample processing be as consistent as possible across all samples for comparison. Samples were collected from multiple locations in the two study counties and processed (centrifugation and aliquotting) at the Moffitt Cancer Center. After drawing, blood samples were immediately chilled for transport to Moffitt in a Styrofoam container accompanied by a frozen pack for overnight delivery. This system allowed centrifugation within 16-28 hours after blood drawing. Centrifugation was at 3,000 g for 20 minutes after which the plasma was immediately aliquoted per each 0.5 cc into coated microEppendorf tubes and immediately frozen at −70° C. Samples were batch-shipped on dry ice by overnight delivery to the Cleveland Clinic for analysis. Shipped samples were identified by a unique sample number only, without identifiers or any indication of the subject's status as ovarian cancer patient or control. The samples were maintained at −70° C. until preparation for mass spectrometry analysis.

LPL Analysis

Lipids were extracted as described previously with minor modifications. Two (2) mL of MeOH/chloroform (2:1) and 0.1 mL of 6 N HCl were added to 0.5 mL plasma. Samples were vortexed for 1 minute and incubated on ice for 10 minutes. 1 mL of chloroform and 1 mL of H2O were added to separate the phases. Samples were vortexed for 0.5 minutes prior to centrifugation (2,000 g for 10 minutes). The lower phase was transferred to a new glass tube. One (1) mL of chloroform was added to the upper phase left in the original tube, to extract more lipids, and the tube was centrifuged (2,000 g for 10 minutes). The lower phase was transferred into the same tube (with the lower phase extract) and the solvent was evaporated under nitrogen at 30° C. The dried lipids were suspended in 50 µL of solvent (MeOH:chloroform, 2:1), vortexed, and applied to a thin-layer chromatography (TLC) plate. Two standards (18:1-LPA and 18:1-LPC) were applied to help in identifying the "LPA band" and the "LPC band" on each TLC plate. The TLC plates were developed in the solvent system (chloroform:MeOH:AmOH, 65:35:5.5) until the solvent front was 1.5 inch from the top of the plate. The lipids from the "LPA band" and the "LPC band" were eluted with 2 mL of MeOH:chloroform (2:1) twice. The lipid solutions were dried under nitrogen at 30° C. and lipids resuspended in 100 µL of MeOH for mass spectrometry.

Mass spectrometry analyses were performed using a Quattro Ultima triple quadrupole ESI-MS (Micromass, Inc., Beverley, Mass.) with the Masslynx data acquisition system. A Waters 2690 (Waters) autosampler was used to introduce the samples into the ESI source. The mobile phase used for all experiments was MeOH:H2O (9:1; v:v) and the flow rate was 100 µL/min. The injection volume was set to 20 µL/sample for all experiments. The positive or negative ion-mode with multiple reaction monitoring (MRM) was used to quantitatively analyze the positively or negatively charged phospholipids. The collision energies were 70 eV in the negative mode and 25 eV in the positive mode. Nitrogen was used as both drying and nebulising gas at flow rates of 500 L/h and 50 L/h, respectively. The ESI probe capillary was held at 3 kV for the positive mode and *3 kV for the negative mode and the cone voltage was set at 35V in positive mode and *50V in negative mode. The source and desolvation temperatures were 100° C. and 200° C., respectively.

LPA and other negatively charged LPL were analyzed in the negative mode with the monitoring ions at m/z 378 (parent ion)-79 (product ion) for S1P, 381-79 for 14:0-LPA, 393-79 for 16:0-Alkenyl-LPA, 395-79 for 16:0-Alkyl-LPA, 409-79 for 16:0-LPA, 421-79 for 18:0-Alkenyl-LPA, 423-79 for 18:0-Alkyl-LPA, 433-79 for 18:2-LPA, 435-79 for 18:1-LPA, 437-79 for 18:0-LPA, 571-79 for 16:0-LPI, 599-79 for 18:0-LPI, and 619-79 for 20:4-LPI, respectively. All lipids with the phosphorylcholine group (positively charged) were analyzed in the positive mode. Monitoring ions were at m/z 465 (parent ion)-184 (product ion) for SPC, 496-184 for 16:0-LPC, 510-184 for 17:0-LPC, 520-184 for 18:2-LPC, 524-184 for 18:0-LPC, 544-184 for 20:4-LPC and 568-184 for 22:6-LPC, respectively. The dwell time in the MRM mode was 0.11 ms and the scan delay was 0.02 s.

Categorical variables were analyzed using Chi-square tests or Fisher's exact tests, depending on sample size. Continuous variables, including univariate comparisons for quantitative variables between normal and cancer cases, were compared using the Student's t-tests, or the Wilcoxon Rank Sum test, depending on the distribution of the variable of interest. Adjustment for potential confounding variables, such as the stage at diagnosis, was carried out by using general linear modeling or analysis of variance methods, as appropriate. Stepwise logistic regression analysis was used to determine the statistical significance of LPA, LPI, LPC (and their subspecies) and S1P. All statistical significance testing was 2-sided, and P values less than 0.05 were considered to be statistically significant. P values in the range of 0.01 to 0.05 should be interpreted with caution because of multiple testing issues. Statistical analyses were performed utilizing SAS Software, SAS Institute Inc, Cary, N.C.

The ages, stages, grades, histologic subtypes and treatment status of the 117 ovarian cancer patients who participated in the study are shown in FIG. 1. A total of 166 samples were analyzed, including 27 from healthy controls, 45 obtained preoperatively from women with ovarian cancer and 94 obtained postoperatively from women with ovarian cancer, with 22 patients having both preoperative and postoperative samples.

Figure 4:
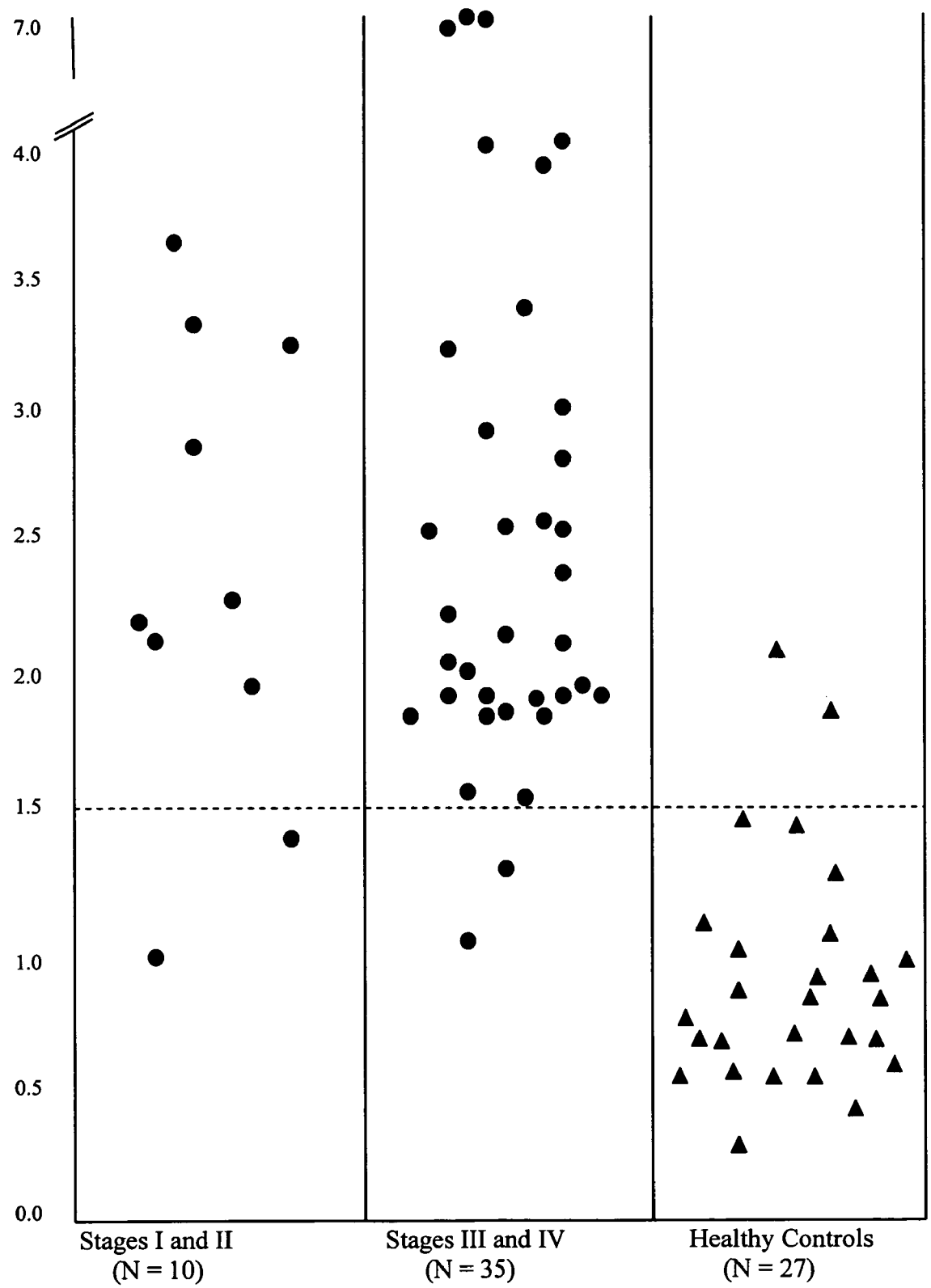
FIG. 4 shows that using an ROC-derived cutoff value of 1.5 µM, total LPA levels achieved 91.7% correct classification, 91.1% sensitivity and 92.6% specificity.

There were statistically significant differences between preoperative case samples (N=45) and control samples (N=27) in the mean levels of several individual LPA species, the combination of 16:0-LPA/20:4-LPA, total LPA, total LPI and S1P (FIG. 2). The best discrimination between samples obtained preoperatively from ovarian cancer patients and those from healthy controls was achieved by the combined levels of 16:0-LPA and 20:4-LPA, with 93.1% correct classification, 91.1% sensitivity and 96.3% specificity (FIG. 3). Receiver operating characteristic curves (ROC) 35 were examined and a cutoff 16:0-/24:0-LPA level of 0.62 µM was identified as optimizing the sensitivity and specificity of the assay (FIG. 3). All patients with preoperative samples had 16:0-/24:0-LPA levels above the 0.62 µM cutoff, with the exception of one stage I patient, one stage II patient and 2 stage III patients. There were no significant differences in mean values for any LPL species between preoperative patients who were pre-menopausal versus postmenopausal. Levels did not correlate with tumor size. Using an ROC-derived cutoff value of 1.5 µM, total LPA levels achieved 91.7% correct classification, 91.1% sensitivity and 92.6% specificity (FIG. 4). All 4 of the cases which had 16:0-/20:4-LPA levels below the 0.62 µM cutoff also had low total LPA levels, as might be expected since total LPA includes 16:0-LPA and 20:4-LPA. Similarly, the control with an elevated 16:0-/20:4-LPA level of 0.91 µM also had the highest total LPA level. CA 125 values were available on 35 of the 45 patients with a preoperative sample. Levels were elevated >30 units in 29 of the 35 patients. Only one of the 6 patients with a normal CA 125 preoperative value also had low (presumed normal) LPA values.

The mean values for the combination of 16:0-LPA/20:4-LPA in the plasma samples obtained preoperatively from patients with stage I, stage II, stage III and stage IV ovarian cancer were 1.23 µM (S.D. 0.52), 0.92 µM (S.D. 0.43), 1.23 µM (S.D. 0.70) and 0.93 µM (S.D. 0.15), respectively, compared with 0.35 µM (S.D. 0.17) for the controls (FIG. 2). The mean values of total LPA in the plasma samples obtained preoperatively from patients with stage I (7 patients), stage II (3 patients), stage III (31 patients) and stage IV (4 patients) ovarian cancer were 2.57 µM (S.D. 0.94), 2.15 µM (S.D. 0.71), 2.93 µM (S.D. 1.77) and 1.97 µM (S.D. 0.27) µM, respectively, compared with 0.90 µM (S.D. 0.43) for 27 healthy controls (Table 2). The mean values of total LPI in the plasma samples obtained preoperatively from patients with stage I, stage II, stage III and stage IV ovarian cancer were 2.98 µM (S.D. 1.57), 4.58 µM (S.D. 2.71), 4.25 µM (S.D. 2.81) and 2.96 µM (S.D. 0.33), respectively, compared with 1.51 µM (S.D. 0.79) for the controls (FIG. 2).

In 22 cases with both preoperative and postoperative samples, the postoperative levels of total LPA, total LPC, 22:6-LPA, 18:0-LPA, the combination of 20:4-LPA/22:6-LPA, 20:4-LPC and 18:2-LPC were significantly lower than preoperative levels (P=0.03, 0.05, 0.02, 0.04, 0.03 0.02, 0.003 and 0.03, respectively) (FIG. 5). Of these LPL, 18:0 LPC, 18:2 LPC and total LPC levels also showed statistically significant differences between preoperative case samples (N=45) and all postoperative case samples (N=94) (P<0.05). There were no statistically significant differences in mean LPL levels between postoperative samples obtained prior to initiation of chemotherapy versus post-chemotherapy.

The reason for the discrepancy between the findings of the two prior studies with interpretable results regarding the utility of LPA as a biomarker for detection of ovarian cancer is unclear. There were many methodologic differences between the two studies, including differences in sample collection, processing and lipid analyses.

It will be seen that the objects set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method of detecting ovarian cancer in a subject comprising the steps of:
obtaining a biological sample from said subject;
measuring the mass of a lysophospholipid in the biological sample, where the mass determines a subspecies of the lysophospholipid where the lysophospholipid subspecies is selected from the group consisting of lysophosphatidic acid (LPA), lysophosphatidylinositol (LPI), lysophosphatidylcholine (LPC) and sphingosine-1-phosphate (S1P); and
quantitatively measuring the amount of the at least one lysophospholipid subspecies,
whereby the presence of elevated levels of the at least one lysophospholipid subspecies is indicative of the presence of ovarian cancer.

2. The method of claim 1 wherein the biological sample is taken preoperatively.

3. The method of claim 2, further comprising taking a biological sample postoperatively and comparing the levels of the at least one lysophospholipid subspecies in the preoperative sample with the levels of the at least one lysophospholipid subspecies in the postoperative sample, whereby the presence of elevated or substantially equal levels of the at least one lysophospholipid subspecies relative to the preoperative biological sample is indicative of recurrence of ovarian cancer.

4. The method of claim 1 wherein the at least one subspecies of lysophosphatidic acid (LPA) is selected from the group consisting of 16:0-LPA, 18:0-LPA, 18:1-LPA, 18:2-LPA, 20:4-LPA, 22:6-LPA, 16:0-A-LPA, 18:0-A-LPA, 16:0-An-LPA, 18:0-An-LPA, and combined 16:0-LPA/20:4-LPA.

5. The method of claim 1, wherein the at least one subspecies of lysophosphatidic acid (LPA) is selected from the group consisting of 16:0-LPA, 20:4-LPA and combined 16:0-LPA/20:4-LPA.

6. The method of claim 1, wherein the at least one subspecies of Lysophosphatidylinositol (LPI) is selected from the group consisting of 16:0-LPI, 18:0-LPI and 20:4-LPI.

7. The method of claim 1, wherein the at least one subspecies of Lysophosphatidylcholine (LPC) is selected from the group consisting of 16:0-LPC, 18:0-LPC, 18:1-LPC, 18:2-LPC, 20:0-LPC, 20:4-LPC and 22:6-LPC.

8. The method of claim 3, wherein the at least one lysophospholipid subspecies is selected from the group consisting of 22:6-LPA, 18:0-LPA, 20:4-LPA/22:6-LPA, 20:4-LPC and 18:2-LPC.

9. The method of claim 1 wherein the mass of the at least one lysophospholipid subspecies is determined by electrospray ionization/mass spectrometry.

10. The method of claim 4, further comprising measuring the amount of LPI.

11. The method of claim 10, further comprising comparing the levels of LPA subspecies against total LPA and LPI.

12. The method of claim 1, wherein the at least one lysophospholipid subspecies is compared to a threshold value, where elevated levels of the lysophospholipid subspecies above a threshold value are indicative of the presence of ovarian cancer.

13. The method of claim 12, wherein the threshold value is 0.62 µM or 1.5 µM.

14. A method of detecting ovarian cancer in a subject comprising the steps of:
obtaining a biological sample from said subject;
measuring the mass of a lysophospholipid in the biological sample, further comprising isolating the lysophospholipid from other components of the biological sample and determining the mass of the lysophospholipid by electrospray ionization/mass spectrometry, where the mass determines a subspecies of the lysophospholipid selected from the group consisting of lysophosphatidic acid (LPA), lysophosphatidylinositol (LPI), lysophosphatidylcholine (LPC) and sphingosine-1-phosphate (S1P); and quantitatively measuring the amount of the at least one lysophospholipid subspecies, whereby the presence of elevated levels of the at least one lysophospholipid subspecies is indicative of the presence of ovarian cancer.

15. The method of claim 14, further comprising measuring the amount of LPI.

16. The method of claim 15, further comprising comparing the levels of LPA subspecies against total LPA and LPI.

17. The method of claim 14, wherein the at least one lysophospholipid subspecies is compared to a threshold value, where elevated levels of the lysophospholipid subspecies above a threshold value are indicative of the presence of ovarian cancer.

18. The method of claim 17, wherein the threshold value is 0.62 µM or 1.5 µM.

* * * * *